United States Patent
Mangold et al.

(10) Patent No.: US 6,872,402 B2
(45) Date of Patent: *Mar. 29, 2005

(54) BACTERICIDAL SILICON DIOXIDE DOPED WITH SILVER

(75) Inventors: Helmut Mangold, Rodenbach (DE); Rainer Golchert, Dieburg (DE)

(73) Assignee: Degussa AG, Düsseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/173,648

(22) Filed: Jun. 19, 2002

(65) Prior Publication Data

US 2003/0235624 A1 Dec. 25, 2003

Related U.S. Application Data

(62) Division of application No. 09/658,505, filed on Sep. 8, 2000, now Pat. No. 6,423,331.

(30) Foreign Application Priority Data

Sep. 9, 1999 (DE) .......................... 199 43 057

(51) Int. Cl.[7] .................. A01N 25/12; A01N 25/08; A01N 59/00; C01B 33/12; C01B 33/18
(52) U.S. Cl. .................. 424/421; 424/417; 424/618; 424/619; 424/724; 423/278; 423/335; 423/336; 423/337; 423/592; 423/606; 423/608; 423/618; 423/625; 514/951
(58) Field of Search ................... 424/421, 417, 424/618–619, 724; 423/278, 335, 336, 337, 592, 606, 608, 618, 625; 514/951

(56) References Cited

U.S. PATENT DOCUMENTS 4,292,290 A  9/1981  Tunison
6,328,944 B1 * 12/2001  Mangold et al. ............ 423/278
6,613,300 B2 *  9/2003  Mangold et al. ............ 423/278

FOREIGN PATENT DOCUMENTS

EP  0 850 876 A1  7/1998
EP  0 995 718 A1  4/2000

OTHER PUBLICATIONS

Chemical abstracts 127:62042 (1997).*
Chemical abstracts 121:91926 (1994).*
Chemical abstracts 119:3066 (1993).*
Akifumi et al., "Optical Waveguides and Manufacture Thereof", STN Database Accession No. 129:60395 CA XP002150667 and JP 10 133043 A (Hitachi Cable, Ltd., Japan) May 22, 1998.
Formenti et al., "Preparation in a Hydrogen–Oxygen Flame of Ultrafine Metal Oxide Particles", J. of Colloid and Interface Science, vol. 39, No. 1 (Apr. 1972), pp. 79–89.
Database WPI, Sec. Ch, Week 199923 Derwent Publications Ltd., London, GB; AN 1999–272888 XP00215264 and JP 11 086757 A (Nippon Electric Glass Co.), Mar. 30, 1999.

* cited by examiner

*Primary Examiner*—John Pak
(74) *Attorney, Agent, or Firm*—Smith, Gambrell & Russell, LLP

(57) ABSTRACT

Pyrogenically prepared silica doped with silver or silver oxide is prepared by feeding an aerosol into a flame such as is used for the preparation of pyrogenic silica, mixing the aerosol homogeneously with gas mixture before the reaction, then allowing the aerosol/gas mixture to react in a flame. The resulting pyrogenic silicas doped with silver or silver oxide are separated from the gas stream. The pyrogenic silica doped with silver or silver oxide by means of an aerosol can be used as a bactericidal filler.

5 Claims, 1 Drawing Sheet

BACTERICIDAL SILICON DIOXIDE DOPED WITH SILVER

CROSS-REFERENCE TO RELATED APPLICATION

This is a divisional of U.S. application Ser. No. 09/658,505, filed on Sep. 8, 2000, which is now U.S. Pat. No. 6,423,331 (issued on Jul. 23, 2002), which claims priority to German Application No. DE 199 43 057.8, filed on Sep. 9, 1999, which disclosure is incorporated herein by reference.

FIELD OF THE INVENTION

The invention relates to a pyrogenically prepared silicon dioxide doped with silver or silver oxide by means of an aerosol and having bactericidal properties, and to a process for its preparation and its use. The invention relates also to use of this doped silicon dioxide in dispersions or as a filler in rubber and silicone rubber.

BACKGROUND OF THE INVENTION

It is known to dope pyrogenically prepared silica in one step in a flame using a special process. (DE 96 50 500 A1). That process is a combination of high-temperature flame hydrolysis with pyrolysis. That doping process is to be distinguished from the older, so-called "co-fumed process", in which the gaseous starting materials (for example $SiCl_4$ gas and $AlCl_3$ gas) are pre-mixed and burnt together in a flame reactor.

SUMMARY OF THE INVENTION

In the doping process, an aerosol is fed into a flame in which a pyrogenic oxide is produced by flame hydrolysis, the aerosol containing a salt of the compound to be doped.

It has now been found that if silver salts dissolved in water are used as the starting material for the aerosol, a doped pyrogenic silica having bactericidal properties is obtained as the product.

The invention provides a pyrogenically prepared silica doped with silver or silver oxide by means of an aerosol. The silica is characterized in that the base component is a silica prepared pyrogenically by flame oxidation or, preferably, by flame hydrolysis. The silica is doped with a doping component of from 0.0001 wt. % up to 20 wt. %, the doping amount preferably being in the range from 1 to 10,000 ppm, and the doping component is a salt or a salt mixture of a silver compound or metallic silver or mixtures thereof. The BET surface area of the doped oxide is from 1 to 600 $m^2/g$, preferably in the range from 40 to 400 $m^2/g$.

The invention further provides a process for the preparation of the pyrogenically prepared silica doped with silver or silver oxide by means of an aerosol, which process is characterized in that an aerosol is fed into a flame such as is used for the pyrogenic preparation of silica by flame oxidation or, preferably, by flame hydrolysis, the aerosol is mixed homogeneously with the gas mixture used for the flame oxidation or the flame hydrolysis before the reaction, then the aerosol/gas mixture is allowed to react in the flame and the resulting pyrogenically prepared silicas doped with silver or silver oxide are separated from the gas stream in a known manner. An aqueous solution containing salts or salt mixtures of silver or the metal itself in dissolved or suspended form or mixtures thereof is used for the preparation of the aerosol. The aerosol is produced by atomization by means of a two-component nozzle or by a different method of aerosol production.

The following may be used as salts: $Ag(NO_3)$, $Ag_2(SO_4)$, $Ag_2O$, or the salts may be complexed with complexing agents or ammonia.

The process of flame hydrolysis for the preparation of pyrogenic oxides is known from Ullmanns Enzyklopädie der techn. Chemie 4th edition, Vol. 21, p. 464.

DETAILED DESCRIPTION OF THE PREFERRED EMBODIMENTS

Figure 1:
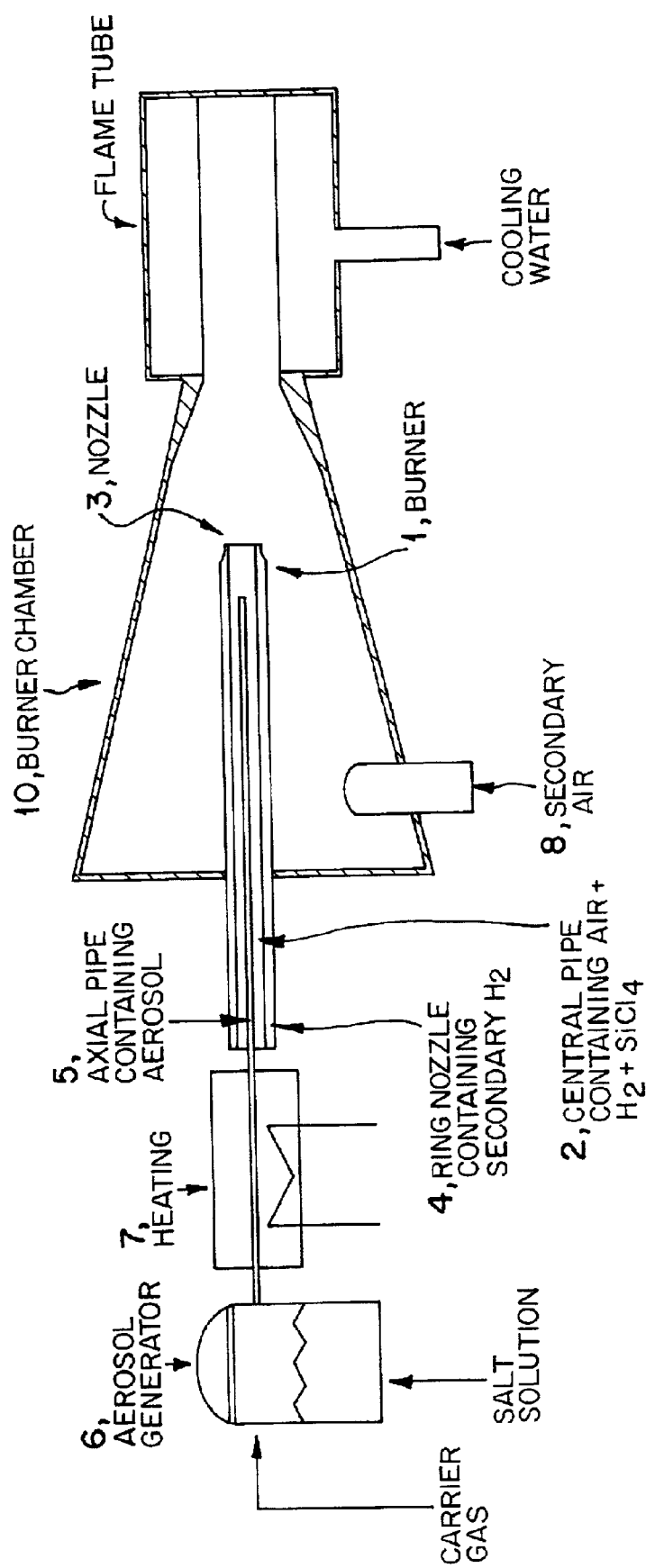
FIG. 1 is a schematic representation of the doping apparatus.

The doped silicon dioxide according to the invention and the process for its preparation and use are described below with reference to FIG. 1 and the following Example.

The core element of the apparatus is a burner of known type for the preparation of pyrogenic oxides.

The burner 1, shown in FIG. 1 includes a central pipe 2 which opens into a nozzle 3 from which the main gas stream flows into the burner chamber 10, in which chamber the gas burns. This inner nozzle 3 is surrounded by a ring nozzle or jacket 4, from which secondary hydrogen flows.

In the central pipe 2 there is a further axial pipe 5, which ends several centimeters before the outlet of the nozzle 3 of the central pipe 2. The aerosol is fed into the axial pipe 5.

The aerosol, which is an aqueous silver salt solution, is produced in an aerosol generator 6, which may be an ultrasonic atomizer.

The silver salt/water aerosol produced in the aerosol generator is passed by means of a light carrier gas stream through a heating zone 7, in which the entrained water vaporizes, leaving small salt crystals in finely divided form in the gas phase.

Secondary air is fed into the burner chamber through inlet 8.

EXAMPLE 1

Preparation of a Pyrogenic Silica Doped with Silver or Silver Oxide 4.44 kg/h of $SiCl_4$ are vaporized at about 130° C. and transferred to the central pipe of a burner of known type. 3 $Nm^3/h$ of primary hydrogen and 7.5 $Nm^3/h$ of air are additionally fed into the central pipe.

The gas mixture flows out of the inner nozzle of the burner and burns in the burner chamber and the water-cooled flame tube adjacent thereto.

0.5 $Nm^3/h$ of secondary hydrogen are fed into the ring nozzle.

12 $Nm^3/h$ of secondary air are additionally fed into the burner chamber.

A second gas stream flows out of the axial pipe 5 into the central pipe 2.

The second gas stream consists of an aerosol which is produced in a separate atomizing unit by ultrasonic atomization. The aerosol generator atomizes 725 g/h of 5% aqueous silver sulfate solution. The silver sulfate aerosol is guided through a heated line with the aid of the carrier gas of 0.5 $Nm^3/h$ of air, the aqueous aerosol being converted at temperatures of about 180° C. into a gas and a salt crystal aerosol.

The reaction gases and the resulting pyrogenic silica doped with silver or silver oxide are drawn through a cooling system by the application of reduced pressure, and the particle gas stream thereby cools to a range of about 100° to 160° C. The solid is separated from the waste gas stream in a filter or cyclone (not shown).

The pyrogenically prepared silica doped with silver or silver oxide is obtained in the form of a finely divided white powder. In a further step, any hydrochloric acid residue still adhering to the silica is removed therefrom at elevated temperature by treatment with air containing water vapor.

The BET surface area of the pyrogenic silica doped with silver is 206 $m^2/g$.

The preparation conditions are summarized in Table 1, further analytical data of the silica so obtained are given in Table 2.

TABLE 1

Experimental conditions for the preparation of pyrogenic silica doped with silver or silver oxide

| $SiCl_4$ kg/h | Primary air $Nm^3/h$ | Sec. air $Nm^3/h$ | $H_2$ core $Nm^3/h$ | $H_2$ jacket $Nm^3/h$ | Salt solution | Aerosol amount kg/h | Air aerosol $Nm^3/h$ | BET $m^2g$ |
|---|---|---|---|---|---|---|---|---|
| 4.44 | 7.5 | 12 | 3 | 0.5 | 5% aqueous $Ag_2SO4$ | 0.725 | 0.5 | 206 |

Explanation: Primary air = amount of air in the central pipe; Sec. air = secondary air; $H_2$ core = hydrogen in the central pipe; Aerosol amount = mass flow rate of the salt solution converted into aerosol form; Air aerosol = amount of carrier gas (air) for the aerosol;

TABLE 2

Analytical data

| | BET $m^2/g$ | pH value 4% sus. | Tamped density g/l | $Ag_2O$ content wt. % |
|---|---|---|---|---|
| Example | 206 | 4.13 | 24 | 1.72 |

Explanation: pH 4% sus. = pH value of the 4% aqueous suspension

Advantages of the silica according to the invention:
The silica according to the invention doped with silver or silver oxide has bactericidal properties.

The pyrogenic silica doped with silver or silver oxide by means of an aerosol can be used as a bactericidal filler especially in the production of paints or coatings, in the paper industry, as a catalytically active substance, as a starting material for the preparation of dispersions, as a polishing material (CMP applications), as a ceramics base material, in the electronics industry, as a filler for polymers, as a starting material for the production of glass or glass coatings or glass fibers, as a release auxiliary even at high temperatures, in the cosmetics industry, as an absorber material, as an additive in the silicone and rubber industry, for adjusting the rheology of liquid systems, for heat protection stabilization, as a heat insulating material, as a flow auxiliary, as a filler in the dental industry, as an adjuvant in the pharmaceuticals industry or in the paint industry.

What is claimed is:

1. A process for the preparation of pyrogenic silica doped with silver or silver oxide, comprising:

vaporizing silicon tetrachloride;

mixing vaporized silicon tetrachloride with hydrogen and air;

preparing an aerosol using as a starting material a salt solution containing salts or salt mixtures of silver or silver metal in dissolved or suspended form or mixtures thereof, the aerosol being produced by atomization by means of a two-component nozzle;

mixing the aerosol homogeneously with a gas mixture used for flame oxidation or flame hydrolysis and the vaporized silicon tetrachloride with hydrogen and air;

feeding the mixture of the aerosol and gas and the vaporized silicon tetrachloride with hydrogen and air into a flame used for preparation of pyrogenic oxides by flame oxidation or flame hydrolysis;

reacting the mixture of aerosol and gas and the vaporized silicon tetrachloride with hydrogen and air in the flame; and separating pyrogenic silica doped with silver or silver oxide from a resulting gas stream.

2. A process according to claim 1, wherein the aerosol is produced in an aerosol generator.

3. A process according to claim 2, wherein the aerosol generator comprises an ultrasonic atomizer.

4. The process according to claim 1, wherein the mixture of aerosol and gas react to form a pyrogenic oxide doped with 0.0001 wt. % to 20 wt. % silver or silver oxide.

5. The process according to claim 1, wherein the separated pyrogenic oxides doped with silver and silver oxide have a BET surface area from 1 to 600 $m^2/g$.

* * * * *